(12) United States Patent
Kratzer

(10) Patent No.: US 7,915,049 B2
(45) Date of Patent: Mar. 29, 2011

(54) METHOD FOR INVESTIGATING THE THROMBOCYTE FUNCTION OF THE BLOOD

(76) Inventor: Michael Kratzer, Munich (DE)

( * ) Notice: Subject to any disclaimer, the term of this patent is extended or adjusted under 35 U.S.C. 154(b) by 1094 days.

(21) Appl. No.: 10/513,815

(22) PCT Filed: May 9, 2003

(86) PCT No.: PCT/DE03/01491
§ 371 (c)(1),
(2), (4) Date: Apr. 7, 2005

(87) PCT Pub. No.: WO03/096012
PCT Pub. Date: Nov. 20, 2003

(65) Prior Publication Data
US 2005/0227361 A1    Oct. 13, 2005

(30) Foreign Application Priority Data

May 10, 2002   (DE) .................................. 102 21 054

(51) Int. Cl.
*G01N 33/48* (2006.01)
*G01N 11/02* (2006.01)
(52) U.S. Cl. ............................ 436/69; 422/73; 73/64.51
(58) Field of Classification Search .................... 436/69; 422/73; 73/64.51
See application file for complete search history.

(56) References Cited

U.S. PATENT DOCUMENTS

| 3,486,859 A | 12/1969 | Sanz et al. |
| 3,674,012 A | 7/1972 | Sage |
| 4,604,894 A * | 8/1986 | Kratzer et al. .............. 73/64.41 |
| 5,800,781 A | 9/1998 | Gavin et al. |
| 5,854,076 A | 12/1998 | Kundu et al. |

FOREIGN PATENT DOCUMENTS

| CA | 1308934 | 10/1992 |
| EP | 0 223 044 | 5/1987 |
| EP | 0 223 244 | 5/1987 |

OTHER PUBLICATIONS

Poiseuilles Law. HyperPhysics. http://hyperphysics.phy-astr.gsu.edu/Hbase/ppois.html.*

* cited by examiner

*Primary Examiner* — Krishnan S Menon
*Assistant Examiner* — Rebecca Fritchman
(74) *Attorney, Agent, or Firm* — Jacobson Holman PLLC

(57) ABSTRACT

A method for investigating the thrombocyte function of the blood, and particularly of platelet aggregation, wherein the following steps are carried out: a) cross-flowing an aperture with blood or blood components; b) determining the active radius of the aperture depending on time and c) evaluating the time-dependent modification of the radius as a measure for blood cell and/or thrombocyte function.

9 Claims, 3 Drawing Sheets

Diameter of the aperture opening (μm)

METHOD FOR INVESTIGATING THE THROMBOCYTE FUNCTION OF THE BLOOD

This is a nationalization of PCT/DE03/01491 filed May 9, 2003 and published in German.

BACKGROUND OF THE INVENTION

1. Field of the Invention

The invention at hand has to do with a technique and a mechanism for testing the thrombocyte function in blood.

2. Description of the Related Art

There are various mechanisms for testing the aggregation of blood platelets or the coagulation of blood. For example, a mechanism is based on the EP 0223244 in which the blood is aspirated through an aperture out from a blood supply space by means of a moveable piston in a cylinder and the pressure in the space between the piston and the aspirated in blood is measured, whereby the piston is driven in such a way that a target pressure value is maintained in the space. The piston movement serves as a measurement for the amount of blood flow.

SUMMARY OF THE INVENTION

The role of the invention at hand consists in creating a technique and a mechanism that enable to get an exact determination of the thrombocyte function in the blood.

This role is performed by a method for testing the thrombocyte function in blood, whereby an aperture with blood or blood components is flowed through, including the steps of determining the effective radius of the aperture as a function of time by measuring the drop in pressure at the aperture as a function of time and determining the blood flow volume through the aperture as a function of time; calculating the hemodynamically effective radius of the aperture by the Hagen-Poiseuille law; and evaluating the time-dependent change in the radius as a measure for the blood cell and/or thrombocyte function. The present invention also includes a mechanism for carrying out this method.

The essential advantage of the invention at hand consists in allowing for an exact determination of the blood platelet delay time by means of which the arterial thrombus growth is controlled or influenced. Thus, since in accordance with the invention it becomes possible to measure the designated blood platelets' delay time, for the first time evidence can be gathered on e.g. existing disease risks, such as arterial thrombotic tendency, for example the risk of myocardial infarction in a patient. For the first time medications can be developed that selectively have an effect on the blood platelet delay time to eliminate such risks.

The determination of the blood platelet delay time in a patient's fresh blood so to speak 'bedside' very quickly (without blood thinners) and on a very small volume of blood can be arrived at by means of a special design of the invention-related mechanism.

With a particularly preferred design of the invention the thrombocyte function can be determined at a very high degree of reproducibility and preciseness fast and with only a little volume of blood.

BRIEF DESCRIPTION OF THE DRAWINGS

Below the invention and its designs will be explained in more detail in connection with the figures. Shown are.

DETAILED DESCRIPTION OF THE PREFERRED EMBODIMENTS

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

The following considerations and realizations led to the inventions. A time-dependent determination of the loading of an aperture by means of blood platelets when flowing through it surprisingly revealed that the aperture closes in a completely defined way, that is in accordance with the straight line depicted in FIG. 2, whose slant 2 dr/dt yields the growth rate. When simultaneously calculating the blood platelets' time-dependent wall shear rate that represents a measurement for blood platelets' transport rate, it was recognized that in time the wall shear rate sharply rises from a low value at first in the area of the aperture. But since the growth rate during this time remains exactly the same, it can be inferred that a blood platelet delay time exists that indicates that time over which the individual blood platelets first allow an adhesion of other blood platelets. In other words each blood platelet "determines" when, i.e. thus after which lag in time or delay time, other platelets may adhere to it. This blood platelet delay time in connection with certain disease risks and with the development of medications is of primary importance. This means that by the invention-related finding of the mentioned rise dr/dt, i.e. therefore the blood platelet delay time, selective evidence on disease risks, e.g. on the risk for myocardial infarction in a patient, can be gathered and for this reason medications can be selectively developed that influence the blood platelet delay time.

Figure 1:
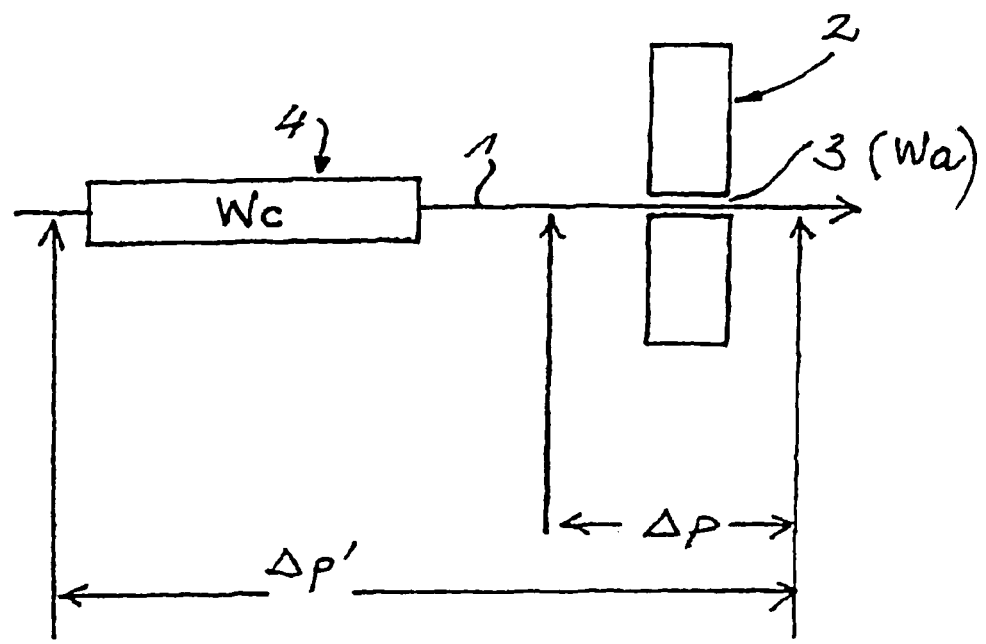
FIG. 1 a mechanism for determining the blood platelet delay time in schematic representation.

FIG. 1 shows an existing mechanism for determining the blood platelet delay time in schematic representation. In essence here according to arrow 1 blood is moved out of a supply space that is not described in any greater detail, for instance via a capillary 4 that forms a blood flow resistance stream Wc, through an aperture 3 of an aperture holder 2. The aperture 3 forms a blood flow resistance Wa.

According to the following equation $$Wa = \frac{\Delta P}{Q} \tag{1}$$

Figure 2:
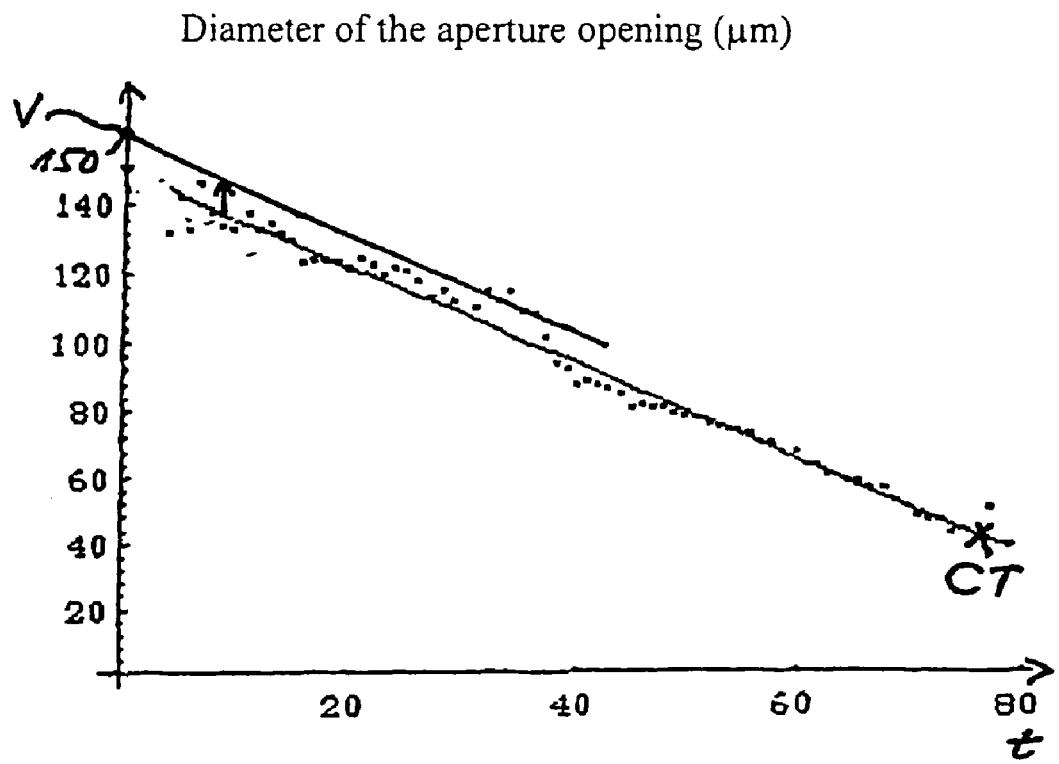
FIG. 2 a diagram for demonstrating the relationship of the aperture diameter to the time, caused due to occlusion by the blood platelets.

($Q$ = volume of blood flow per time)

as well as according to the Hagen-Poiseuille law $$Wa = \frac{8\mu l}{\pi} \cdot \frac{1}{r^4} \tag{2}$$

by time-dependent calculation of the resistance Wa the effective hemodynamic radius of the aperture 3 in accordance with the equation $$r = \sqrt{\frac{8\mu l}{\pi} \cdot \frac{1}{Wa}} \tag{3}$$

can be calculated and spread over time in accordance with FIG. 2.

In equations 1 through 3:
Δp designates the drop in pressure at the aperture, Wa the flow resistance of the aperture, μ the viscosity of the blood flowing through the aperture, l the gauge of the aperture and r the radius of the same.

In FIG. 2 it can be seen that the opening of the aperture 3 quite definitely closes as a function of time surprisingly in accordance with a straight line with a constant slope of (dr/dt=const) with a very high value of statistical probability: e.g. RSq=0.982. If a platelet diameter of 2 μm is assumed, a platelet delay time of 2/0.7=2.8 sec is obtained. With a first control person with normal platelet function a platelet delay time of 2.77+0.32 sec. was determined. The number of measurements was 11. With a second control person the platelet delay time amounted to 2.65+0.1 sec. with 11 measurements and a normal platelet function as well.

Instead of the drop in pressure Δp at the aperture 3 the drop in pressure Δp' can be measured at the capillary 4 and the aperture 3, whereby then the capillary 4 flow resistance Wc has to be deducted to determine the growth rate.

Figure 3:
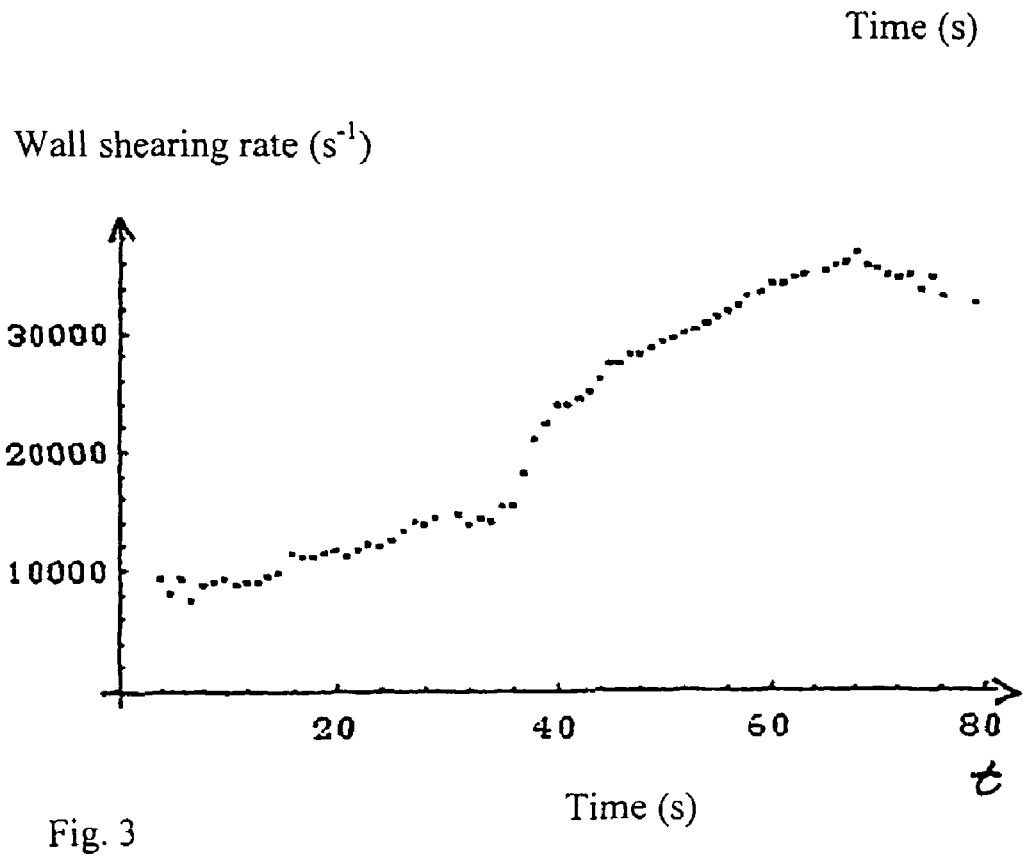
FIG. 3 a diagram for demonstrating the wall shear rate as a function of time.

According to the formula:

$$\gamma w = \frac{4Q}{\pi r^3} \tag{4}$$

the wall shear rate γω in the area of the aperture can be calculated and spread in a time-dependent fashion like FIG. 3. The result is that the platelets' transport rate on the thrombus that is approximately proportional to the wall shear rate rises during the measuring by the factor 4. During this rise though, just as in FIG. 2, the thrombus growth rate remains exactly the same. The inference is that the individual blood platelets in the area of the aperture 3 determine in accordance with a platelet delay time when other blood platelets may adhere to them. The blood platelet delay time, therefore, matches the time difference between a blood platelet's adhesion on the wall of the aperture 3 or on another blood platelet and the adhering of an additional blood platelet.

Figure 4:
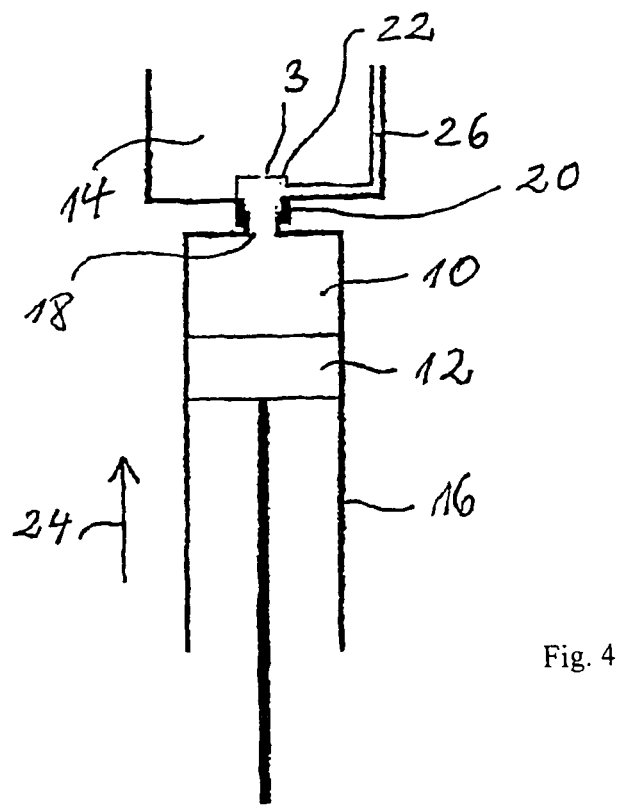
FIG. 4 a mechanism designed as a disposable part for implementing the invention-related technique in schematic representation.

FIG. 4 illustrates a design of the mechanism at hand in schematic representation, wherein blood from a blood supply space 10 is pressed or conveyed with the assistance of a piston 12 through the aperture 3 into a blood collecting space 14. The blood supply 10 is preferably designed in a cylinder 16 in which the piston 12 is arranged pushable. The piston/cylinder arrangement 12, 16 can for this purpose have the shape of a blood withdrawal syringe, wherein the blood supply space 10 is filled when withdrawing blood from a patient's vein. After removing the withdrawal cannula the forward end 18 of the piston/cylinder arrangement 12,16 can be connected with the section encompassing the blood collection space 14 that is preferably designed as a disposable or single use section, wherein the part of its access opening 20 that is connectable to the piston/cylinder arrangement 12, 16 has an aperture holder 22 with the aperture 3 down stream, through which the blood traverses from the blood supply space 10 into the blood collecting space 14 upon activation of the piston 12 in the direction of the arrow 24.

A capillary (in FIG. 1: reference symbol 4) can be placed upstream to aperture 3, as is already familiar.

To measure the pressure reduction on the aperture 3, the disposable section can have a passage 26 that is connected to a pressure meter mechanism in a gauge when taking readings and that runs inside or along its wall from outside to the space upstream of aperture 3.

One advantage here is that after withdrawing blood, for instance at the patient's bed, the disposable section for carrying out the technique at hand can be connected directly to the piston/cylinder arrangement 12, 16 that serves for withdrawal of blood and along with the piston/cylinder arrangement 12, 16 put into the gauge that implements the technique at hand and activates the piston 12.

It should be pointed out that for measuring with a small volume of blood (e.g. in pediatrics) it can be advantageous when carrying out the technique at hand not to activate the piston 12 continuously, but rather jerkily, whereby, for example, the movement of the piston 12 is interrupted at intervals that could be on the order of 3 seconds.

Only one segment of the straight-line dr/dt in FIG. 2 can also be measured, e.g. for measuring with little blood, whereby the corresponding bleeding time can be determined by extrapolating.

Since it is known that a straight-line is to be determined, measurements with stark deviations can be recognized as erroneous and corrected by extrapolating in the areas of deviation. Furthermore, it can also be sufficient to determine only a segment of the straight-line and not to determine measured areas by extrapolating. For example, this can be carried out to save time.

Since the platelet delay time is not dependent on the capillary resistance in the case of using a capillary, capillary errors do not enter into the measurement, thus the measurement precision and reliability can be enhanced.

Below a variation on the invention-related technique is explained in more detail in connection with FIG. 5, by which is possible a particularly advantageous and clear and significant assessment for the user or measurement of the thrombocyte function with a relatively small volume of blood, with short measuring times and an even greater reproducibility.

Figure 5:
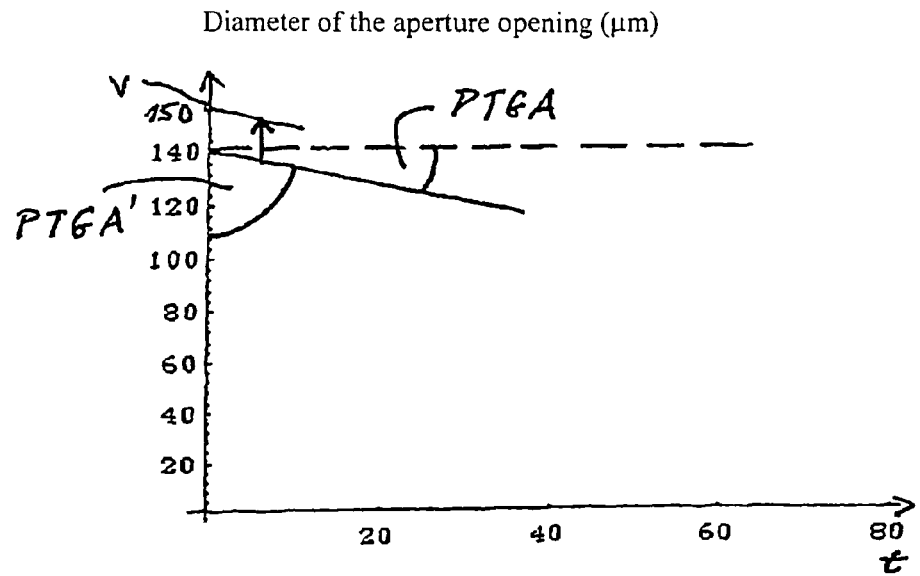
FIGS. 5 and 6 preferred designs of the invention.
Figure 6:
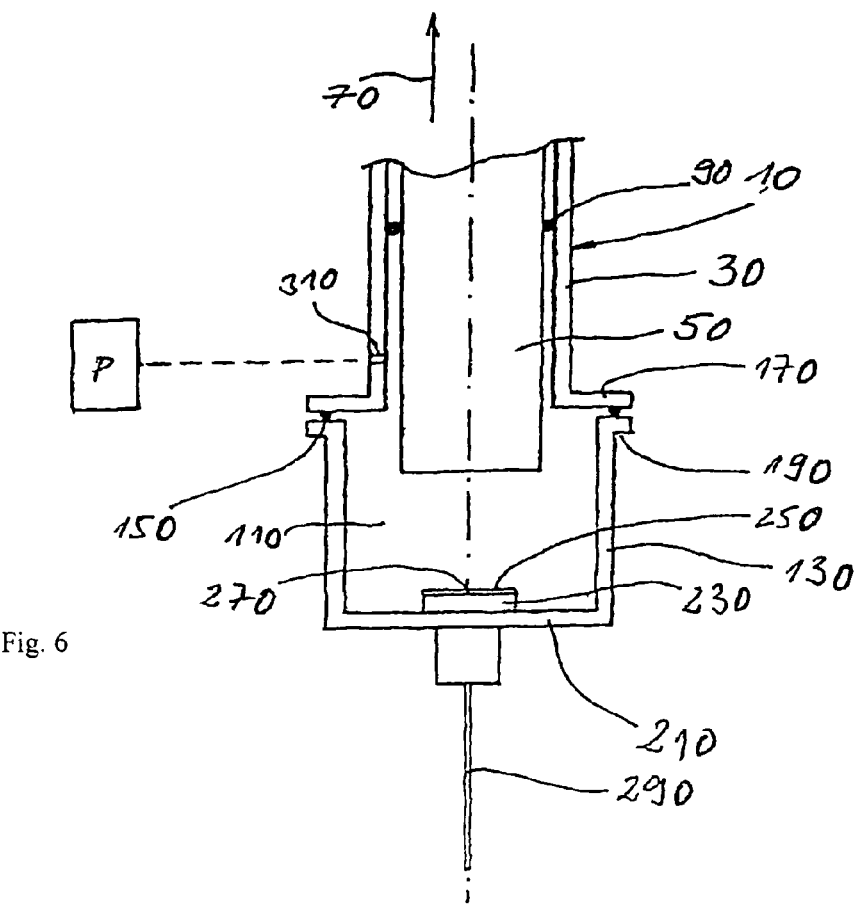

These advantages are achieved due to the fact that by this variation the slope of the straight-lines dr/dt is indeed determined, yet no value CT of the bleeding time is extrapolated, but rather the PTGA angle (Platelet Thrombus Growth Angle) that exists between the straight-line and the t-axis (see FIG. 5). This is particularly advantageous if this angle is relatively small and the straight-line for this reason runs flat, as is the case with a very slow thrombus formation in the aperture 3 which applies e.g. to a taking of medication (for example, aspirin) In this case enormous fluctuations in the CT value would result by the technique explained above even with small deviations of the slope dr/dt of the straight-line. These fluctuations are all the greater the farther the CT value is removed from the t-axis zero point. In such a case the determination or indication PTGA angle is more significant since it is not subjected to the designated fluctuation. Furthermore, this PTGA angle can be derived very fast from the straight-line's slope determined at the start of a measurement by the formula indicated below, thus the measuring time can be relatively short and an only relatively small volume of blood is needed for measuring.

$$\text{PTGA} = -(((\text{arc Tan}(dr/dt))/(\pi/2))90) \tag{5}$$

Determined.

Accordingly even the PTGA' angle can be determined by the formula:

$$\text{PTGA'} = 90 - \text{PTGA} \tag{6}$$

and applied.

The thrombocyte function can, as already mentioned, be quickly established by this variation of the invention at hand, i.e. even with a small volume of blood, particularly also with relatively long thrombus formation times in the aperture 3, as this is possible, for example, with influences of medications, e.g. with the taking of aspirin. Here the values of the PTGA or PTGA' angles determined are to a certain extent comparatively significant because they are not subjected to such great fluctuations as the CT values determined.

A still more improved measurement is made possible with an additional variation of the technique at hand, according to which a fit operation is performed to compensate for changes in blood viscosity and/or the resistance Wc of capillary 4 (FIG. 1). Here with a value t=0 the start value of the aperture opening is always set or fitted to a pre-established defined value V (from e.g. 150 μm in the FIGS. 2 and 5) in such a way that the straight-line at the beginning of a measurement is calculated by extrapolating up to the zero point of the t-axis and the value thereby determined for t=0 shifted to the per-established value V. Proceeding from this value V then the straight-line is determined and the CT value according to FIG. 2 or the PTGA or PTGA' angle according to FIG. 5. In this way the measurement data can be further enhanced because fluctuations in viscosity or the capillary resistance are compensated.

Below an additional variation of the technique at hand is explained by which a quality control of the determined straight-line or the determined PTGA or PTGA' angle is effected. In so doing, as indicated earlier above, it is determined how precisely the measured values dr/dt line on a straight-line or not. With deviations of a pre-established number of values beyond a prescribed measure the corresponding measurement is deemed not processable or corrected.

With certain disease condition or under the influence of medication there may be deviations from the linear relation dr/dt. For example, in the FIG. 2 by means of a pointed line is depicted that the slope of the straight-line during a measurement can change in such a way the straight-line can encompass two segments of varying slopes dr1/dt and dr2/dt, whereby the point of intersection P of these segments is to be ascribed for a certain thrombus formation that is established by certain disease pattern. In such cases the point P is very significant for which reason it is determined with the measurement.

Below an additional preferred form of implementation of the technique at hand is explained in more detail. This essentially has a piston/cylinder arrangement 10 that encompasses a cylinder 30 and a piston 50. The piston 50 can be moved in the direction of the arrow 70, i.e. therefore in its axial direction in the cylinder 30 by means of drive that is not illustrated in any more detail.

The piston 50 preferably has the shape of a metal part polished on its outer surface that consists in particular of stainless steel and possesses the shape of a lengthwise cylindrical rod section. Between the outer surface of the piston 50 and the inner surface of the cylinder 30 that also preferably consists of stainless steel is arranged an O-ring gasket 90 that preferably consists of a rubber material. Since the outer surface of the piston 50 is polished between the gasket 90 and the piston 50 there is extremely little friction so that a jerk-free movement of the piston 50 in the direction of the arrow 70 is assured.

With its end away from the drive that is not illustrated in more detail the piston 50 extends out into a blood uptake space 110 that is established by means of a beaker-shaped vessel 130 that is positioned tightly up against the cylinder 30 with its upper edge area adjacent to the piston 50 with the aid of a gasket 150. For this reason the cylinder 30 has a flange section 170 that extends radially outwards and on the upper edge of the vessel 130 a flange section 190 that protrudes toward the outside radially as well, whereby the O-ring gasket 150 is kept between the flange section 170 and 190 and connects the latter tightly to each other. On the bottom 210 of the vessel 130 an aperture holder 230 is located that holds a platelet 250 or the like with an aperture 270 arranged in it, whereby a capillary 290 led from outside through the bottom part 210 in an inherently familiar way ends shortly prior to the aperture 270 in such a way that out of a blood supply space (not shown) blood that has been aspirated in through the capillary 290 with the movement of the piston 50 in the direction of the arrow 70 is taken in through the aperture 270 into the uptake space 110. The aperture 270 can also be designed and arranged in another way. For example, the end of the capillary 290 that protrudes through into the uptake space 11 can form it.

One pressure-measuring mechanism P that is not illustrated in greater detail is connected to a passageway 310 preferably in the wall of the cylinder 30 for measuring the pressure outside of the blood that has been aspirated through the aperture 270 into the uptake space 110. In this way it is achieved that the vessel 130 is fastened to the aperture holder 230 and the capillary 290 and can be designed as a so-called disposable part and via the gasket 150 optionally to the piston/cylinder arrangement 11 in the simplest way.

It should be pointed out that instead of determining the drop in pressure at the aperture 3 an electrical resistance also could be established by application of a potential difference for determining the hemodynamic resistance of the aperture 3. The radius of the aperture 3 that just exists can also be optically determined.

The invention being thus described, it will be apparent that the same may be varied in many ways. Such variations are not to be regarded as a departure from the spirit and scope of the invention, and all such modifications as would be recognized by one skilled in the art are intended to be included within the scope of the following claims.

The invention claimed is:

1. A method for determining a platelet aggregation function in blood of a patient comprising:
    a) flowing blood through an aperture;
    b) measuring a drop in pressure at the aperture as a function of time;
    c) measuring a blood flow volume through said aperture as a function of time;
    d) determining a flow resistance of the aperture based on said pressure drop and blood flow volume measurements taken in steps b) and c);
    e) determining a viscosity of the blood;
    f) calculating a hemodynamically effective radius of the aperture from said flow resistance by the Hagen-Poiseuille law;
    g) determining a change in said hemodynamically effective radius over time, said change being substantially linear so as to be a generally straight line having a slope (dr/dt);
    h) assuming a prescribed blood platelet diameter; and
    i) correlating the slope (dr/dt) of the substantially linear time dependent change in said hemodynamically effective radius with said blood platelet diameter to establish a platelet delay time as a measure of the rate of said platelet aggregation which provides an indication of possible risks to the patient relating to blood coagulation.

2. The method according to claim 1, further comprising determining a value for closure time (CT), in which the aperture is closed by blood cell or thrombus formation to a given degree, as the measure for the platelet aggregation from the determined straight-line.

3. The method according to claim 2, wherein the closure time value (CT) is pre-established for a radius of the value zero.

4. The method according to claim 1, wherein a platelet thrombus growth angle (PTGA) existing between the determined straight-line and an axis for time (t) is established as a measure for the platelet aggregation function.

5. The method according to claim 1, wherein a second platelet thrombus growth angle (PTGA') existing between the determined straight-line and an axis for the aperture radius (r) is established as a measure for the platelet aggregation function.

6. The method according to claim 1, wherein a value of one selected section of the straight-line is determined by measurement, and at least one other section of the straight-line is determined by extrapolating on the basis of the selected straight-line section.

7. The method according to claim 6, wherein a value of the straight-line at a point time zero (t=0) is determined and the straight-line is shifted by changing parameters in the Hagen-Poiseuille law in such a way that the value of the aperture radius (r) at the point time zero (t=0) corresponds to a pre-established value (V).

8. The method according to claim 1, wherein said change in said hemodynamically effective radius over time results in a plurality of substantially straight-line segments, a point of intersection (P) of two or more of said substantially straight-line segments of varying slopes (dr1/dt; dr2/dt) determining a measure for certain processes in thrombus formation.

9. The method according to claim 1, further comprising calculating the correlation of measuring points with a mathematical function for the quality control of a measurement.

* * * * *